United States Patent
Kokin et al.

(10) Patent No.: US 7,566,806 B2
(45) Date of Patent: Jul. 28, 2009

(54) ALKYLAMINO GROUP-TERMINATED FLUOROETHER AND PROCESS FOR PRODUCING THE SAME

(75) Inventors: Keisuke Kokin, Kitaibaraki (JP); Takehiro Sonoi, Kitaibaraki (JP); Kimihiko Urata, Kitaibaraki (JP)

(73) Assignee: Unimate Co., Ltd., Tokyo (JP)

( * ) Notice: Subject to any disclaimer, the term of this patent is extended or adjusted under 35 U.S.C. 154(b) by 0 days.

(21) Appl. No.: 11/991,049

(22) PCT Filed: Aug. 9, 2006

(86) PCT No.: PCT/JP2006/315713

§ 371 (c)(1), (2), (4) Date: Feb. 26, 2008

(87) PCT Pub. No.: WO2007/026513

PCT Pub. Date: Mar. 8, 2007

(65) Prior Publication Data

US 2008/0221360 A1 Sep. 11, 2008

(51) Int. Cl.
- *C07C 209/08* (2006.01)
- *C07C 217/04* (2006.01)
- *C07C 217/08* (2006.01)
- *C07C 217/26* (2006.01)

(52) U.S. Cl. ................. 564/481; 564/503; 564/504; 564/505; 564/508

(58) Field of Classification Search .......... None
See application file for complete search history.

(56) References Cited

FOREIGN PATENT DOCUMENTS

| JP | 04-178357 | 6/1992 |
| JP | 2001-011032 | 1/2001 |
| JP | 2003-137844 | 5/2003 |

OTHER PUBLICATIONS

Maruzen, Jikken Kagaku Koza 20 Yuki Gosei II—Alchol Amine, the Chemical Society of Japan 4th Edition, pp. 284-288 (Jul. 6, 1992).
Abulikemu et al. improved Synthesis of Perfluoroctylpropyl Amine J. of Flourine Chemistry 125 pp. 1143-1146 (2004).
Szlavik et al., "Convenient Syntheses and Characterization of Fluorophilic Perfluoroctyl-Propyl Amines and Ab Initio Calculations of Proton Affinities of Related Model Compounds" J. of Fluorine Chemistry pp. 7-14 (2001).

*Primary Examiner*—Brian J Davis
(74) *Attorney, Agent, or Firm*—Butzel Long

(57) ABSTRACT

An alkylamino group-terminated fluoroether compound, represented by the following general formula:

$$RfO[CF(CF_3)CF_2O]_mCF(CF_3)(CH_2)_nNR^1R^2$$

(where Rf is a perfluoro lower-alkyl group, $R^1$ is an alkyl group having 1-12 carbon atoms, $R^2$ is a hydrogen atom, or an alkyl group having 1-12 carbon atoms, m is an integer of 0-10, and n is an integer of 3-8) is a novel compound, and is produced by reaction of an iodide-terminated fluoroether compound, represented by the following general formula:

$$RfO[CF(CF_3)CF_2O]_mCF(CF_3)(CH_2)_nI$$

with an alkylamine compound, represented by the following general formula:

$$NHR^1R^2.$$

5 Claims, No Drawings

ALKYLAMINO GROUP-TERMINATED FLUOROETHER AND PROCESS FOR PRODUCING THE SAME

RELATED APPLICATIONS

The present application is a 35 U.S.C. §371 national stage filing of International Patent Application No. PCT/JP2006/315713, filed Aug. 9, 2006, to which priority is claimed under 35 U.S.C. §120 and through which priority is claimed under 35 U.S.C. §119 to Japanese Priority Patent Application No. 2005-248920, filed Aug. 30, 2005.

TECHNICAL FIELD

The present invention relates to an alkylamino group-terminated fluoroether and a process for producing the same, and more particularly to a novel alkylamino group-terminated fluoroether having a flexibility in the molecular chain due to the presence of an ether linkage and applicable as an effective raw material for synthesis, and a process for producing the same.

BACKGROUND ART

No prior art examples of synthesizing a fluoro polyoxoalkylamine have been so far disclosed, but one example of synthesizing perfluoroalkylalkylamine given below:

In the reaction, $NHR^1R^2$, where $R^1$, $R^2$=H, $CH_3$, is allowed to react with perfluorooctylpropyl iodide to obtain the desired perfluorooctylpropyl-amine in a high yield.

Non-Patent Literature 1: J. Fluorine Chem. 108, pp 7-14 (2001)

A process, which comprises subjecting 3-perfluorooctyl-propanol $CF_3(CF_2)_6CF_2(CH_2)_3OH$ to Dess-Martin oxidation in a $CH_2Cl_2$ solvent to convert the terminated $CH_2OH$ group to a CHO group, followed by reaction with benzylamine in the presence of a $NaBH(OCOCH_3)_3$ catalyst in a tetrahydrofuran solvent, then by a silica gel chromatographical treatment to obtain

and finally by reaction with hydrogen under one atmospheric pressure in the presence of a Pd/C catalyst in a diethyl ether/n-hexane mixed solvent to obtain

has been also reported. The process needs not only a long series of steps, but also necessary to use a special boron reagent and a chlorine-based solvent, making the process unsuitable for the industrial scale synthesis.

Non-Patent Literature 2: J. Fluorine Chem., 125, pp 1143-1146 (2004)

Another process for producing a fluoroalkylamine in a high yield by efficient amination of fluoroalkyl halide using ammonia in the presence of an iodine compound has been proposed, but the process inherently involves such problems as (1) difficult of availability of perfluoroalkyl chloride or bromide as a starting raw material, (2) the structures of the perfluoroalkyl halides are restricted by boiling points, etc. and thus have no such a high universal applicability as to allow the industrial scale production, (3) difficult removal of high boiling point aprotonic polar solvents used as reaction solvents such as N-methylpyrrolidone, and N,N-dimethylimidazolidinone after the reaction, and (4) all of the compounds are compounds having a perfluoroalkyl group in the tetrafluoroethylene skeleton, which are compounds capable of forming perfluorooctanoic acid in the ecological system now at issue, and thus are not preferable from the environmental viewpoint.

Patent Literature 1: JP-A-2003-137844

DISCLOSURE OF THE INVENTION

Problem to be Solved by the Invention

An object of the present invention is to provide a novel alkylamino group-terminated fluoroether having a flexibility in the molecular chain due to the presence of a ether linkage and applicable as an effective raw material for synthesis, and also to provide a process for producing the same.

Means for Solving the Problem

The present invention provides an alkylamino group-terminated fluoroether compound, represented by the following general formula:

(where Rf is a perfluoro lower-alkyl group, $R^1$ is an alkyl group having 1-12 carbon atoms, $R^2$ is a hydrogen atom, or an alkyl group having 1-12 carbon atoms, m is an integer of 0-10, and n is an integer of 3-8) as a novel compound.

The present alkylamino group-terminated fluoroether compound can be produced by reaction of a iodide-terminated fluoroether compound, represented by the following general formula:

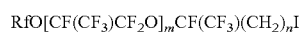

with an alkylamine compound represented by the following general formula:

Effect of the Invention

The present novel alkylamino group-terminated fluoroether compound has a flexibility in the molecular chain due to the presence of ether linkage oxygen atoms in the molecule, different from the so far reported fluoroalkylamines, and thus various functionalities based on the flexibility can be expected. The fluorooxoalkylamine has a high reactivity in comparison of the corresponding alcohol, and an expectable broad application field as industrial raw materials, etc. by formation of complexes with various metals.

The present fluoroether compound can be readily produced by reaction of the corresponding iodide-terminated fluoroether compound with an alkylamine compound, and thus the present process is suitable for the industrial-scale production.

BEST MODES FOR CARRYING OUT THE INVENTION

An iodide-terminated fluoroether compound as a starting raw material for the production of the present alkylamino group-terminated fluoroether compound having the following general formula:

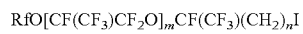

can be readily obtained by reaction of the corresponding hydroxyl group-terminated fluoroether compound having the following general formula:

$$RfO[CF(CF_3)CF_2O]_mCF(CF_3)(CH_2)_nOH$$

with KI, etc. in the presence of a phosphoric acid catalyst.

In the formulae, Rf is a perfluoro lower-alkyl group such as perfluoromethyl group, perfluoroethyl group, perfluoropropyl group, etc., m is 0-10, preferably 0-4, and n is 3-8, preferably 3-4, depending on the hydroxyl group-terminated fluoroether compound.

An alkylamine compound, $NHR^1R^2$, for use in the reaction with the iodide-terminated fluoroether compound is any of monoalkylamine and dialkylamine, which can be selected appropriately in view of uses. The alkyl group has 1-12, preferably 1-4 carbon atoms.

The alkylamine compound can also serve as a trapping agent for hydrogen iodide by-produced by the reaction at the same time and thus can be used in an amount of 2 parts by mole or more, preferably 3-8 parts by mole, more preferably 4-7 parts by mole on the basis of one part by mole of fluoropolyoxoalkyl iodide as the raw material at the time of reaction.

For the reaction between these two reactants an ordinary solvent can be used without any particular restriction, so far as the reaction solvent is inert to such a substitution reaction as in the present invention. Generally, an ether-based solvent such as tetrahydrofuran, furan, dioxane, diethylene glycol dimethyl ether, etc. can be used. In view of the cost and easy removal of the solvent after the reaction, it is preferable to use tetrahydrofuran having an appropriate boiling point (66° C.).

The reaction temperature depends on the kind of reaction solvent to be used, and generally in a wide temperature range from room temperature to the boiling point of a reaction solvent. Practically, it is preferable that the reaction temperature is from room temperature to about 70° C. The reaction pressure can be either the atmospheric pressure or superatmospheric pressure. When an alkylamine compound having a relatively high boiling point is used in the reaction under the atmospheric pressure, it is preferable to use a reactor provided with a reflux condenser to enhance a reactor operating efficiency, whereas when an alkylamine compound having a lower boiling point than room temperature, that is, in a gaseous form, is used, and when the reaction is to be conducted under the atmospheric pressure, it is preferable to continuously add the alkylamine compound to the reaction solution of fluorooxoalkyl iodide, for example, by bubbling, or else a pressure vessel is used to conduct the reaction under a superatmospheric pressure.

EXAMPLES

The present invention will be described in detail below, referring to Examples.

Example 1

172 g (217 millimoles) of iodide-terminated fluoroether compound (99.4 GC %) having the following chemical formula:

$$CF_3CF_2CF_2O[CF(CF_3)CF_2O]_2CF(CF_3)(CH_2)_3I$$

and 900 ml of tetrahydrofuran were charged into a four-necked flask having a net capacity of 2 L, provided with a reflux condenser, a dropping funnel, a thermometer, and a stirrer, in a nitrogen atmosphere, and 52 g (1.13 moles) of monopropylamine (100 GC %) was slowly added thereto at room temperature from the dropping funnel, while stirring the reaction mixture. After the dropwise addition, the reaction mixture was stirred at room temperature for further one hour, followed by further stirring with heating at the inside temperature of 60° C. for 5 hours. Then, the tetrahydrofuran was distilled off under a subatmospheric pressure, and the resulting white crystals were separated by filtration, whereby 149.4 g (yield: 95%) of monopropylamino group-terminated fluoroether compound (99.0 GC %) having the following chemical formula was obtained.

$$CF_3CF_2CF_2O[CF(CF_3)CF_2O]_2CF(CF_3)(CH_2)_3NH(C_3H_7)$$

Furthermore, simple distillation was carried out for decoloration, whereby 145.2 g (distillation yield: 97%) of the desired compound of 99.2 GC % was obtained.

$^1$H-NMR ((CD$_3$)$_2$CO,TMS):δ 0.97(t,J$_{HH}$=7.33 Hz, C$\underline{H}_3$) 1.27(N$\underline{H}$)
1.40~1.50(m, —NCH$_2$C$\underline{H}_2$CH$_3$)
1.54~1.71(m, —CH$_2$C$\underline{H}_2$CH$_2$—)
2.39~2.51(m, —CF(CF$_3$)C$\underline{H}_2$—)
2.56(t,J$_{HH}$=7.15 Hz, —NHC$\underline{H}_2$CH$_2$CH$_3$)
2.69(t,J$_{HH}$=6.42 Hz, —C$\underline{H}_2$NHCH$_2$CH$_2$CH$_3$)
$^{19}$F-NMR((CD$_3$)$_2$CO,CFCl$_3$):ppm  −144.0~143.6(—C$\underline{F}$(CF$_3$)CF$_2$—)
−128.5(CF$_3$C$\underline{F}_2$CF$_2$O—)
−125.9(J$_{HF}$=149 Hz, —C$\underline{F}$(CF$_3$)CH$_2$—)
−82.2(C$\underline{F}_3$CF$_2$CF$_2$O—)
−81.9~−77.3(—CF(CF$_3$)C$\underline{F}_2$O—, —C$\underline{F}_2$O—)
−78.9(—CF(C$\underline{F}_3$)CF$_2$O—)
−78.2(—CF(C$\underline{F}_3$)CH$_2$—)

Example 2

170 g (215 millimoles) of iodide-terminated fluoroether compound (99.4 GC %) having the following chemical formula:

$$CF_3CF_2CF_2O[CF(CF_3)CF_2O]_2CF(CF_3)(CH_2)_3I$$

and 900 ml of tetrahydrofuran were charged into a four-necked flask having a net capacity of 2 L, provided with a reflux condenser, a dropping funnel, a thermometer, and a stirrer, in a nitrogen atmosphere, and 109 g (1.07 moles) of dipropylamine (100 GC %) was slowly added thereto at room temperature from the dropping funnel, while stirring the reaction mixture. After the dropwise addition, the reaction mixture was stirred at room temperature for further two hours, followed by further stirring with heating at the inside temperature of 60° C. for 7 hours. Then, the tetrahydrofuran was distilled off under a subatmospheric pressure, and the resulting white crystals were separated by filtration, whereby 152.5 g (yield: 92%) of dipropylamino group-terminated fluoroether compound (98.5 GC %) having the following chemical formula was obtained.

$$CF_3CF_2CF_2O[CF(CF_3)CF_2O]_2CF(CF_3)(CH_2)_3N(C_3H_7)_2$$

Furthermore, simple distillation was carried out for decoloration, whereby 148.7 g (distillation yield: 98%) of desired compound of 99.0 GC % was obtained.

The invention claimed is:
1. An alkylamino group-terminated fluoroether compound, represented by the following general formula:

$$RfO[CF(CF_3)CF_2O]_mCF(CF_3)(CH_2)_nNR^1R^2$$

where Rf is a perfluoro lower-alkyl group, $R^1$ is an alkyl group having 1-12 carbon atoms, $R^2$ is a hydrogen atom or an alkyl group having 1-12 carbon atoms, m is an integer of 0-10, and n is an integer of 3-8.

2. A process for producing an alkylamino group-terminated fluoroether compound according to claim 1, wherein an iodide-terminated fluoroether compound, represented by the following general formula:

$$RfO[CF(CF_3)CF_2O]_mCF(CF_3)(CH_2)_nI$$

where Rf is a perfluoro lower-alkyl group, m is an integer of 0-10, and n is an integer of 3-8
   is allowed to react with an alkylaniline compound, represented by the following general formula:

$$NHR^1R^2$$

where $R^1$ is an alkyl group having 1-12 carbon atoms, and $R^2$ is a hydrogen atom or an alkyl group having 1-12 carbon atoms.

3. A process for producing an alkylamino group-terminated fluoroether compound according to claim 2, wherein the alkylamine compound is used in an amount of 2 parts be mole or more on the basis of one part by mole of the iodide-terminated fluoroether compound.

4. A process for producing an alkylamino group-terminated fluoroether compound according to claim 2, wherein the reaction is carried out in the presence of an ether-based solvent.

5. A process for producing an alkylamino group-terminated fluoroether compound according to claim 4, wherein the ether-based solvent is tetrahydrofuran.

* * * * *

UNITED STATES PATENT AND TRADEMARK OFFICE
CERTIFICATE OF CORRECTION

| | |
|---|---|
| PATENT NO. | : 7,566,806 B2 |
| APPLICATION NO. | : 11/991049 |
| DATED | : July 28, 2009 |
| INVENTOR(S) | : Keisuke Kokin et al. |

Page 1 of 1

It is certified that error appears in the above-identified patent and that said Letters Patent is hereby corrected as shown below:

On the Title Page, item [30] should be inserted

The Foreign Application Priority Data information is erroneously omitted.

The Foreign Application Priority Data should be added to show --Aug. 30, 2005 (JP) 2005-248920--.

Signed and Sealed this

Thirty-first Day of August, 2010

David J. Kappos
*Director of the United States Patent and Trademark Office*